(12) United States Patent
Li et al.

(10) Patent No.: US 11,795,785 B2
(45) Date of Patent: Oct. 24, 2023

(54) DEVICE FOR MEASURING STRATUM DEFORMATION DURING NATURAL GAS HYDRATE EXPLOITATION

(71) Applicant: GUANGZHOU INSTITUTE OF ENERGY CONVERSION, CHINESE ACADEMY OF SCIENCES, Guangzhou (CN)

(72) Inventors: Xiaosen Li, Guangzhou (CN); Yi Wang, Guangzhou (CN); Zhaoyang Chen, Guangzhou (CN); Zhiming Xia, Guangzhou (CN); Yu Zhang, Guangzhou (CN); Gang Li, Guangzhou (CN)

(73) Assignee: GUANGZHOU INSTITUTE OF ENERGY CONVERSION, CHINESE ACADEMY OF SCIENCES, Guangzhou (CN)

( * ) Notice: Subject to any disclaimer, the term of this patent is extended or adjusted under 35 U.S.C. 154(b) by 474 days.

(21) Appl. No.: 17/059,252

(22) PCT Filed: Sep. 8, 2020

(86) PCT No.: PCT/CN2020/114084
§ 371 (c)(1),
(2) Date: Nov. 26, 2020

(87) PCT Pub. No.: WO2021/159695
PCT Pub. Date: Aug. 19, 2021

(65) Prior Publication Data
US 2022/0228464 A1    Jul. 21, 2022

(30) Foreign Application Priority Data

Aug. 6, 2020 (CN) .......................... 202010783624.0

(51) Int. Cl.
*E21B 41/00* (2006.01)
*G01B 11/16* (2006.01)
(Continued)

(52) U.S. Cl.
CPC ............ *E21B 41/0099* (2020.05); *G01B 7/24* (2013.01); *G01B 11/16* (2013.01); *G01N 33/24* (2013.01)

(58) Field of Classification Search
CPC ....... E21B 41/0099; G01B 11/16; G01B 7/24; G01N 33/24
(Continued)

(56) References Cited

U.S. PATENT DOCUMENTS 7,028,772 B2    4/2006 Wright et al.
2003/0006563 A1*  1/2003 Cater ................... F16J 15/3456
                                                                     277/549
(Continued)

FOREIGN PATENT DOCUMENTS

CN    101550816 A  * 10/2009
CN    101963057 A  *  2/2011
(Continued)

OTHER PUBLICATIONS

Translation CN_103257079 (Year: 2013).*
(Continued)

*Primary Examiner* — Mischita L Henson
*Assistant Examiner* — Monica S Young
(74) *Attorney, Agent, or Firm* — Bayramoglu Law Offices LLC

(57) ABSTRACT

A device for measuring stratum deformation caused by natural gas hydrate dissociation is provided. The device is configured to be disposed inside a natural gas hydrate reactor, wherein the natural gas hydrate reactor is configured to simulate natural gas hydrate formation layers in the
(Continued)

natural gas hydrate reactor, and the natural gas hydrate formation layers include a superstratum layer, a sediment layer and a substratum layer from top to bottom. The device includes a displacement sensor fixing plate, displacement sensors and a flexible elastic plate. A plurality of displacement sensors are provided and evenly distributed, wherein a first end of each displacement sensor is fixed to the displacement sensor fixing plate and a second end of each displacement sensor is stretchably and sealingly fixed to the flexible elastic plate. The flexible elastic plate is tightly attached to the superstratum layer.

5 Claims, 5 Drawing Sheets

(51) Int. Cl.
  *G01B 7/24* (2006.01)
  *G01N 33/24* (2006.01)
(58) Field of Classification Search
  USPC .................................................. 73/118.01
  See application file for complete search history.

(56) References Cited

U.S. PATENT DOCUMENTS

| 2009/0084189 A1* | 4/2009 | McMechan ............. G01N 3/12 73/803 |
| --- | --- | --- |
| 2013/0188452 A1 | 7/2013 | St-Onge et al. |
| 2016/0251943 A1* | 9/2016 | Li ............................ B01J 12/02 422/162 |
| 2016/0305205 A1* | 10/2016 | Li ........................ G01N 33/241 |
| 2021/0003517 A1* | 1/2021 | Song ....................... G01N 3/12 |

FOREIGN PATENT DOCUMENTS

| CN | 103257079 A | * | 8/2013 | ............. E21B 43/00 |
| --- | --- | --- | --- | --- |
| CN | 104153760 A | | 11/2014 | |
| CN | 105403672 A | * | 3/2016 | |
| CN | 107045054 A | * | 8/2017 | ................ B01J 3/03 |
| CN | 107269270 A | | 10/2017 | |
| CN | 107991164 A | * | 5/2018 | ............... G01N 3/00 |
| CN | 108386164 A | * | 8/2018 | ................ B01J 3/03 |
| CN | 109372499 A | * | 2/2019 | ............. E21B 49/00 |
| CN | 109752256 A | * | 5/2019 | |
| CN | 111411943 A | | 7/2020 | |
| CN | 111982699 A | * | 11/2020 | ......... G01N 15/0826 |
| CN | 111411943 B | * | 8/2021 | ............. E21B 43/01 |
| CN | 114509532 A | * | 5/2022 | .......... B01J 19/1806 |
| JP | 2000121741 A | | 4/2000 | |

OTHER PUBLICATIONS

Translation CN-109372499 (Year: 2019).*
Translation CN-101550816 (Year: 2009).*
Translation CN-101963057 (Year: 2011).*

* cited by examiner

DEVICE FOR MEASURING STRATUM DEFORMATION DURING NATURAL GAS HYDRATE EXPLOITATION

CROSS REFERENCE TO THE RELATED APPLICATIONS

This application is the national stage entry of International Application No. PCT/CN2020/114084, filed on Sep. 8, 2020, which is based upon and claims priority to Chinese Patent Application No. 202010783624.0, filed on Aug. 6, 2020, the entire contents of which are incorporated herein by reference.

TECHNICAL FIELD

The present invention relates to the field of measurement devices for natural gas hydrate exploitation, and particularly relates to a device for measuring stratum deformation during natural gas hydrate exploitation.

BACKGROUND

The exploitation of natural gas hydrates will affect the mechanical behaviors of sediments, which may induce geological disasters such as stratum subsidence and slope slippage. This is a major safety issue for the exploitation of natural gas hydrates, and thus it is of great practical significance to analyze the mechanical behaviors of hydrate sediments. So far, studies on stratum deformation caused by natural gas hydrate dissociation are mostly carried out using the triaxial test method, in which the analysis of stratum deformation is realized by simulating the stratum conditions through applying axial pressure and confining pressure, and calculating the subsidence based on volume changes during hydrate dissociation. This method is effective for the analysis of stratum deformation but usually conducted through small-scale experiments. When experiments are scaled up, the method would be inapplicable since large-scale dissociation of natural gas hydrates will bring about greater deformation, which is currently one of the biggest challenges in measurement; moreover, as the reactor is scaled up, the subsidence presented in one dimension is insufficient for reflecting the irregularity of deformation during hydrate dissociation. For large-scale experimental system of natural gas hydrates, the deficiencies of existing technology mainly include: it is impossible to measure the stratum deformation throughout a large area; it is impossible to measure a large-scale stratum deformation; it is difficult to conduct the measurements of stratum deformation in more than one dimension.

SUMMARY

One object of the present invention is to overcome the above-mentioned deficiencies of prior art, by providing a device for measuring stratum deformation caused by natural gas hydrate dissociation, and particularly for measuring stratum deformation caused by large-scale dissociation of natural gas hydrates.

In order to realize the above object, the technical solutions of the present invention comprise:

A device for measuring stratum deformation caused by natural gas hydrate dissociation, configured to disposed inside a natural gas hydrate reactor; the reactor is configured to simulate natural gas hydrate formation layers therein, and the formation layers include a superstratum layer, a sediment layer and a substratum layer from top to bottom; the device comprises a displacement sensor fixing plate, displacement sensors and a flexible elastic plate; the displacement sensors are provided in a multiple amount and evenly distributed, wherein one end of each displacement sensor is fixed to the displacement sensor fixing plate and the other end of each displacement sensor is stretchably and sealingly fixed to the flexible elastic plate; the flexible elastic plate is tightly attached to the superstratum layer, and the displacement sensor fixing plate is fixedly disposed in the reactor.

Furthermore, the device comprises an intelligent terminal, wherein data collected by the displacement sensor is transmitted to the intelligent terminal.

Furthermore, the flexible elastic plate is a thin rubber piston.

Furthermore, the thin rubber piston comprises a piston frame and a rubber piston plate whose periphery is sealingly fixed to the piston frame.

Furthermore, the thin rubber piston further comprises a rubber insert, a piston gasket, and a clip; the piston gasket is embedded in a groove of the piston frame; the periphery of the rubber piston plate is sealingly fixed to a lower surface of the piston frame through the rubber insert; the clip is embedded between the rubber insert and the lower surface of the piston frame, and configured to connect the piston frame to the rubber piston plate.

Furthermore, the intelligent terminal is a computer, a tablet computer, or a mobile phone.

Furthermore, the displacement sensors are linear variable differential transformer (LVDT) displacement sensors.

Furthermore, the clip is made of a non-metallic material.

Compared with the prior art, the present invention has the following beneficial effects.

The device not only allows the measurements of stratum deformation caused by large-scale dissociation of natural gas hydrates, but also overcomes the limitation of measurements in only one dimension and realizes the three-dimensional measurements of stratum deformation.

Reference signs: 1—displacement sensor fixing plate; 2—displacement sensor; 3—thin rubber piston; 4—directional-control ball valve; 5—wellbore discharge pipeline; 6—first camera; 7—endoscopic-camera tube; 8—second camera; 9—second lamp; 10—scaled sight glass for observing settled sands; 11—first lamp;

31—piston frame; 32—rubber piston plate; 33—rubber insert; 34—piston gasket; 35—clip;

51—sight glass; 100—reactor; 1001—superstratum layer; 1002—sediment layer; 1003—substratum layer; 1004—wellbore.

Figure 6:
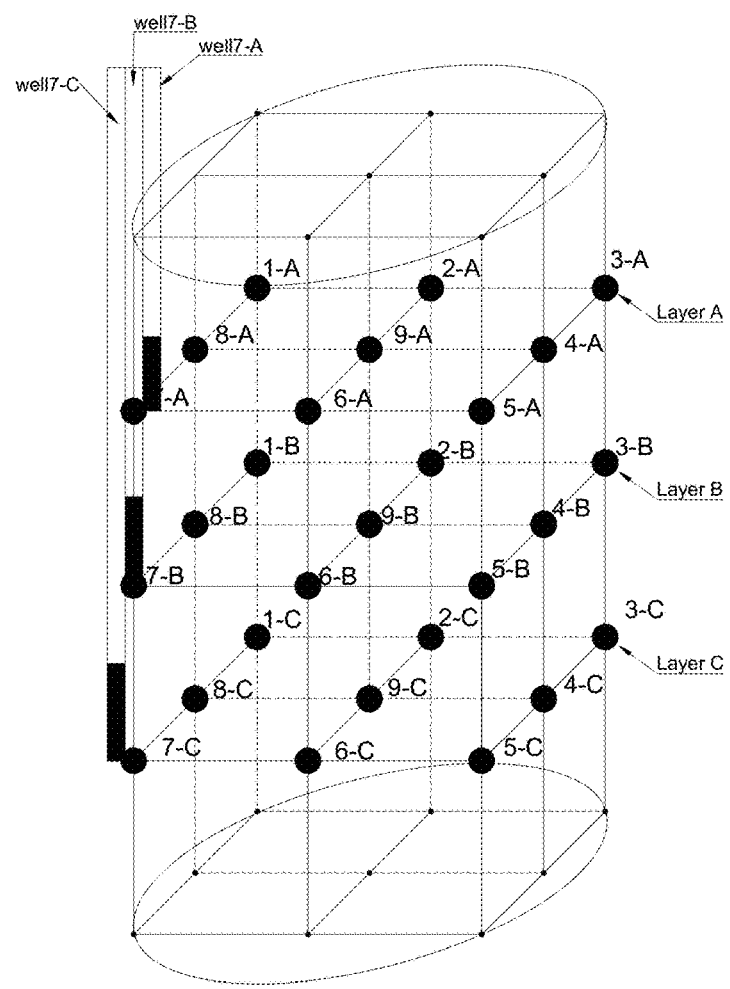

FIG. 6 shows the distribution of wells in the reactor in one embodiment.

Figure 7:
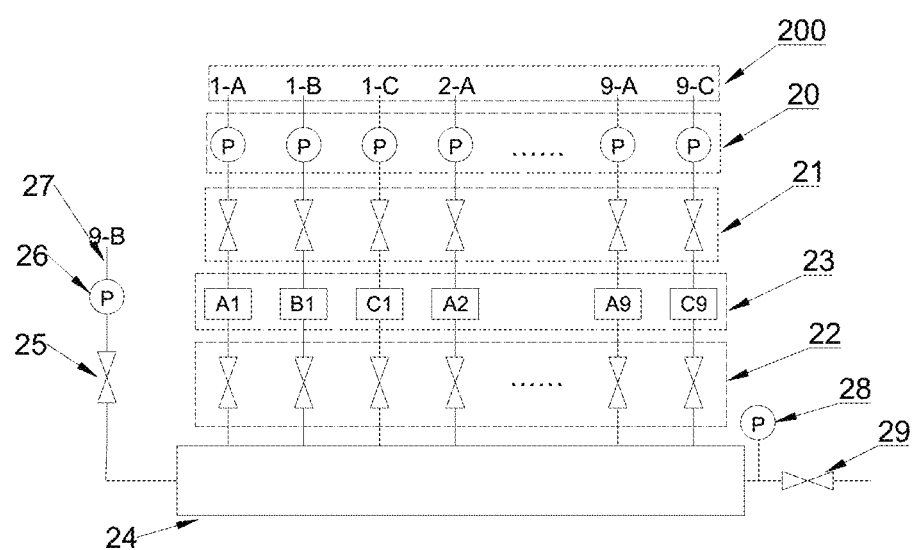

FIG. 7 shows the composition of a flow field measurement device.

Reference signs: 20—non-central vertical well pressure sensor; 21—non-central vertical well outlet valve; 22—communicating vessel valve; 23—differential pressure sensor; 24—communicating vessel; 25—central vertical well outlet valve; 26—central vertical well pressure sensor; 27—central vertical well outlet pipeline; 28—communicating vessel pressure sensor; 29—gas injection valve; 200—non-central vertical well outlet pipeline.

DETAILED DESCRIPTION OF THE EMBODIMENTS

In the description of the present invention, it should be noted that, unless otherwise clearly specified and limited, the terms such as "provide" and "connect" should be understood in a broad sense; for example, a connection can be a fixed connection, a detachable connection, or an integration connection, it can also be a mechanical connection, an electrical connection, or a signal connection, and it can also be a direct connection, an indirect connection through an intermediate medium, or an internal connection between two components. For those of ordinary skill in the art, the specific meaning of the above terms in the present invention should be understood depending on specific circumstances. The technical solution of the present invention will be further described below in combination with the drawings and embodiments.

Figure 1:
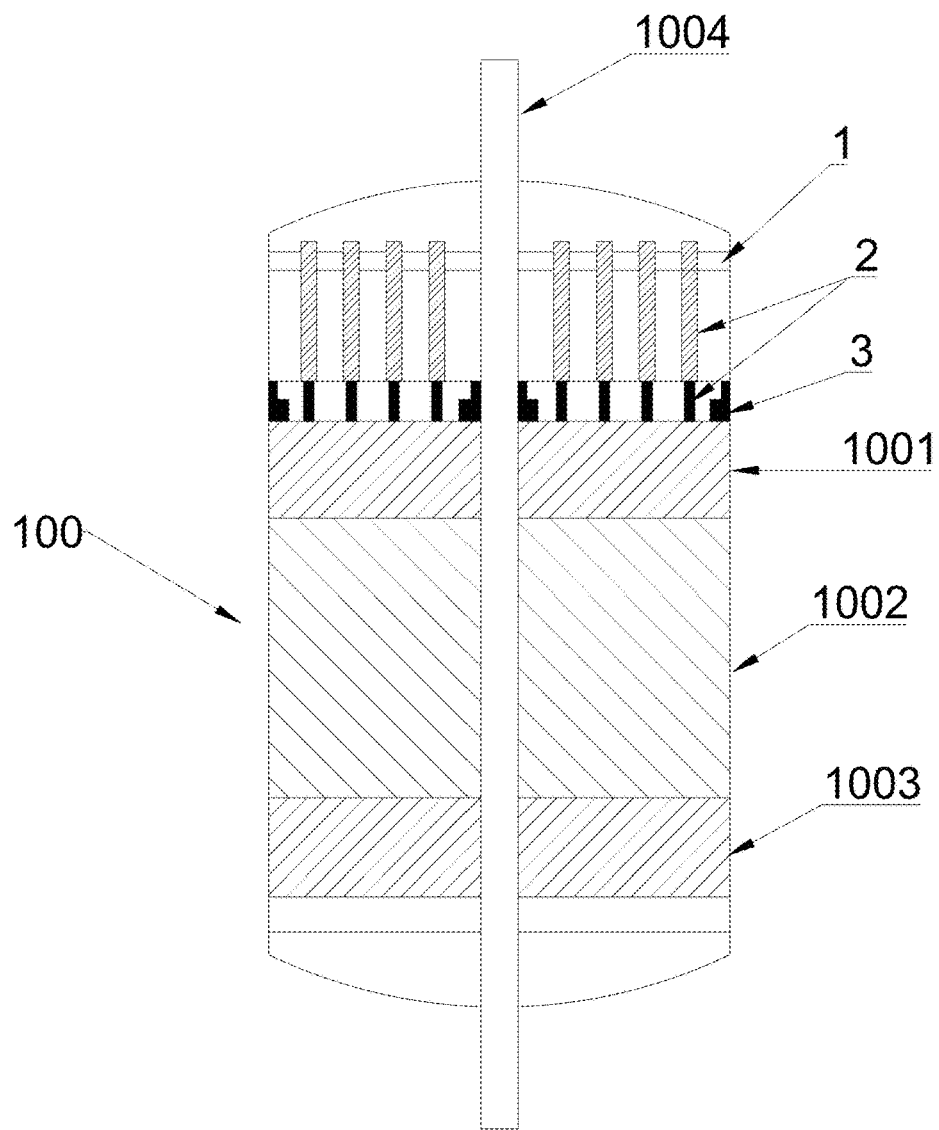
FIG. 1 is a sectional view showing a device of the present invention disposed inside a reactor in one embodiment.
Figure 2:
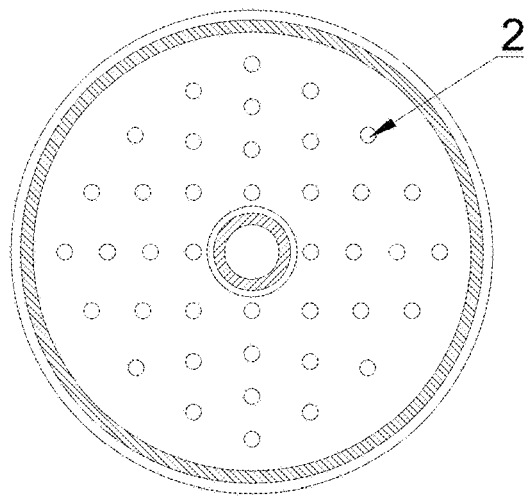
FIG. 2 shows the distribution of displacement sensors.
Figure 3:
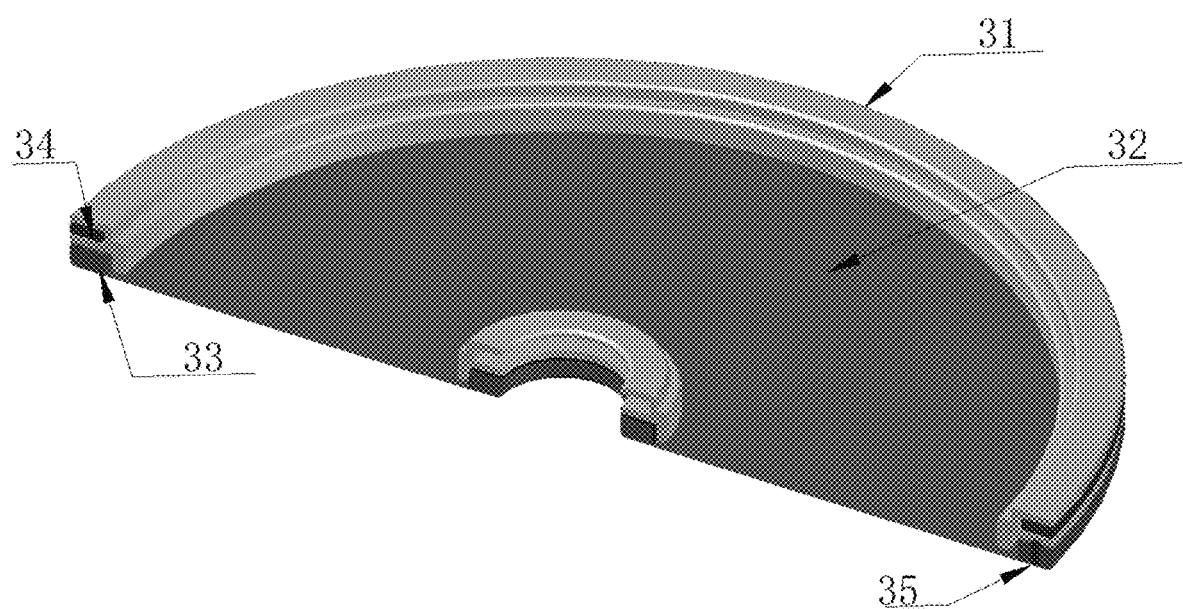
FIG. 3 shows the structure of a thin rubber piston.

As shown in FIG. 1 to FIG. 3, the device for measuring stratum deformation caused by natural gas hydrate dissociation, provided in the present embodiment, is configured to disposed inside a natural gas hydrate reactor 100; the reactor 100 is configured to simulate natural gas hydrate formation layers therein, and the formation layers include a superstratum layer 1001, a sediment layer 1002 and a substratum layer 1003 from top to bottom. As shown in FIG. 1 is a sectional view of the reactor, wherein a simulation wellbore 1004 is dispose in the middle of the reactor 100 and penetrates the reactor 100. The device comprises a displacement sensor fixing plate 1, displacement sensors 2 and a flexible elastic plate. As shown in FIG. 2, the displacement sensors 2 are provided in a multiple amount and evenly distributed, wherein one end of each displacement sensor 2 is fixed to the displacement sensor fixing plate 1 and the other end of each displacement sensor 2 is stretchably and sealingly fixed to the flexible elastic plate; the flexible elastic plate is tightly attached to the superstratum layer 1001, and the displacement sensor fixing plate 1 is fixedly disposed in the reactor 100.

With such configuration, deformation will take place when natural gas hydrate dissociation occurs in the sediment layer, affecting stability of the superstratum layer and causing shape change of the superstratum layer; the flexible elastic plate, which connect the displacement sensors and the superstratum layer, will change its shape along with the deformation of the superstratum layer, which therefore accurately transmits the subsidence deformation of the superstratum layer to the displacement sensors.

For a large-scale natural gas hydrate experimental system, the constructed formation will be large in area while the dissociation of natural gas hydrates involves uncertainties, and therefore subsidence deformation will not be uniform throughout entire area. In the present measurement device, sufficient displacement sensors are connected to the flexible elastic plate over the superstratum layer, which allows the measurement of subsidence deformation at each spot, and therefore realizes the measurement of stratum deformation throughout a large area. By combining the subsidence deformation data of all spots to form an uneven surface from the underlying deformation, it is possible to overcome the limitation of measurements in only one dimension and realize the three-dimensional measurements of stratum deformation.

In view of the above, the device of the present embodiment not only allows the measurements of stratum deformation caused by large-scale dissociation of natural gas hydrates, but also overcomes the limitation of measurements in only one dimension and realizes the three-dimensional measurements of stratum deformation.

In one preferred embodiment, the device further comprises an intelligent terminal (not shown in the drawings), wherein data collected by the displacement sensor can be transmitted to the intelligent terminal, such that real-time online analysis of the stratum deformation data can be realized by the intelligent terminal. The intelligent terminal can be a computer, a tablet computer, or a mobile phone; specifically in the present embodiment, it is a computer.

Specifically, the above-mentioned flexible elastic plate is a thin rubber piston 3; being constructed in the form of the thin rubber piston 3 ensures its tightness to the reactor 100. The thin rubber piston 3 comprises a piston frame 31 and a rubber piston plate 32 whose periphery is sealingly fixed to the piston frame 31. The thin rubber piston further comprises a rubber insert 33, a piston gasket 34, and a clip 35; the piston gasket 34 is embedded in a groove of the piston frame 31; the periphery of the rubber piston plate 32 is sealingly fixed to a lower surface of the piston frame 31 through the rubber insert 33, and the clip 35 is embedded in the rubber insert 33. In the case of large-scale subsidence, if the periphery of the rubber piston plate 32 is fixed, the extent of deformation may reach or even exceed the deformation limit of the rubber piston plate 32, such that it is impossible to precisely measure the stratum deformation, or even, the rubber piston plate will be damaged. Thus, in the present embodiment, the periphery of the rubber piston plate 32 is sealingly fixed to the piston frame 31 having the piston gasket 34; when the scale of subsidence is large, the rubber piston plate 32 will deform downward under force, and when the extent of deformation is too large, the rubber piston plate 32 will move downward and thereby the rubber insert 33 will be compressed; since the non-metallic clip 35 is connecting the piston frame 31 and the rubber piston plate 32, the compressed rubber insert 33 will pull the non-metallic clip 35 to move downward, and then the non-metallic clip 35 will pull the piston frame 31 to move downward. Accordingly, when the scale of subsidence is large, the rubber piston plate 32 will compress the rubber insert 33, and the rubber insert 33, through the non-metallic clip 35, pulls the piston frame 31 to reciprocate; thereby the displacement measured by each displacement sensor 2 is the displacement of the piston plus the displacement of each spot on the rubber piston plate 32, which greatly increases the measurement range of stratum subsidence, or in other words, enables the precise measurement of stratum deformation of large-scale subsidence.

Specifically, the displacement sensors 2 are high-accuracy LVDT displacement sensors, Abek LCA50. Measurement range: 0 to 50 mm. Measurement resolution: 0.001 mm. Measurement accuracy: <±0.2% FS.

In view of the above, compared with the prior art, the device of the present embodiment has the following technical advantages:
  (1) The device, provided with the sufficient displacement sensors, enables the measurement of stratum deformation caused by large-scale dissociation of natural gas hydrates.

(2) The measurement range is high, which is the sum of the piston range and the elastic limit of the rubber piston plate.

(3) The device enables the measurement of curved surface of stratum deformation caused by natural gas hydrate dissociation, so as to realize a three-dimensional measurement of stratum deformation, since it is provided with multiple measurement spots while the rubber piston plate which is sufficiently flexible and thin realizes separate measurement of each spot.

(4) The device has high tightness and is resistant to high pressure, and thereby it will not affect the natural gas hydrate experimental system; since the rubber piston plate is resistant to high pressure, the piston gasket can provide effective tightness during reciprocating motion of the piston frame.

(5) The natural gas hydrate experimental system has improved in safety, as the design of thin rubber piston not only increases the measurement range, but also provides effective protection to the rubber piston plate. Without such design, when the scale of stratum deformation is large, the rubber piston plate will be excessively deformed, and will be even destroyed when it reaches the elastic limit, resulting in damage to the experimental system.

(6) The measurement accuracy is improved. Such improvement is realized through the increased amount of measurement spots, and also through the design of thin rubber piston which effectively improves the measurement accuracy when the extent of subsidence reaches the elastic limit of the rubber piston plate where the rubber piston plate may fail to sensitively reflect the subsidence.

In addition, as the existing technology does not allow the visual observation of the formation of natural gas hydrates inside the reactor, at present in the field of natural gas hydrate, visual observation technology is developed for the purpose of inspecting the formation, distribution, and dissociation of natural gas hydrates, which is realized by disposing a sight glass on the wall of a reactor, introducing a camera into the wellbore and towards the reactor to film the distribution of hydrates in porous media, providing transparent water bath and reactor for small-scale experiment, or using imaging technologies such as XRD and CT. It is difficult to film the distribution of hydrates in porous media, since the hydrates are covered by the media. Transparent reactors are expensive, thus not suitable for most conditions. The X-ray CT imaging technology relies on the density variations inside the measured object, while hydrates are mainly composed of natural gas (mainly methane molecules) and water molecules which are similar in molecular weight and thus cannot be distinguished by X-ray CT, resulting in low accuracy for imaging the phase state of natural gas hydrates. The use of camera in wellbore is still an immature technology. Furthermore, the visual inspection of several properties during hydrate exploitation, such as multiphase flow and sand production, inside the wellbore, is still not realized; the existing systems do not allow the real-time observation of outlet flow; the visual observation and measurement of settled sands are ignored.

Figure 4:
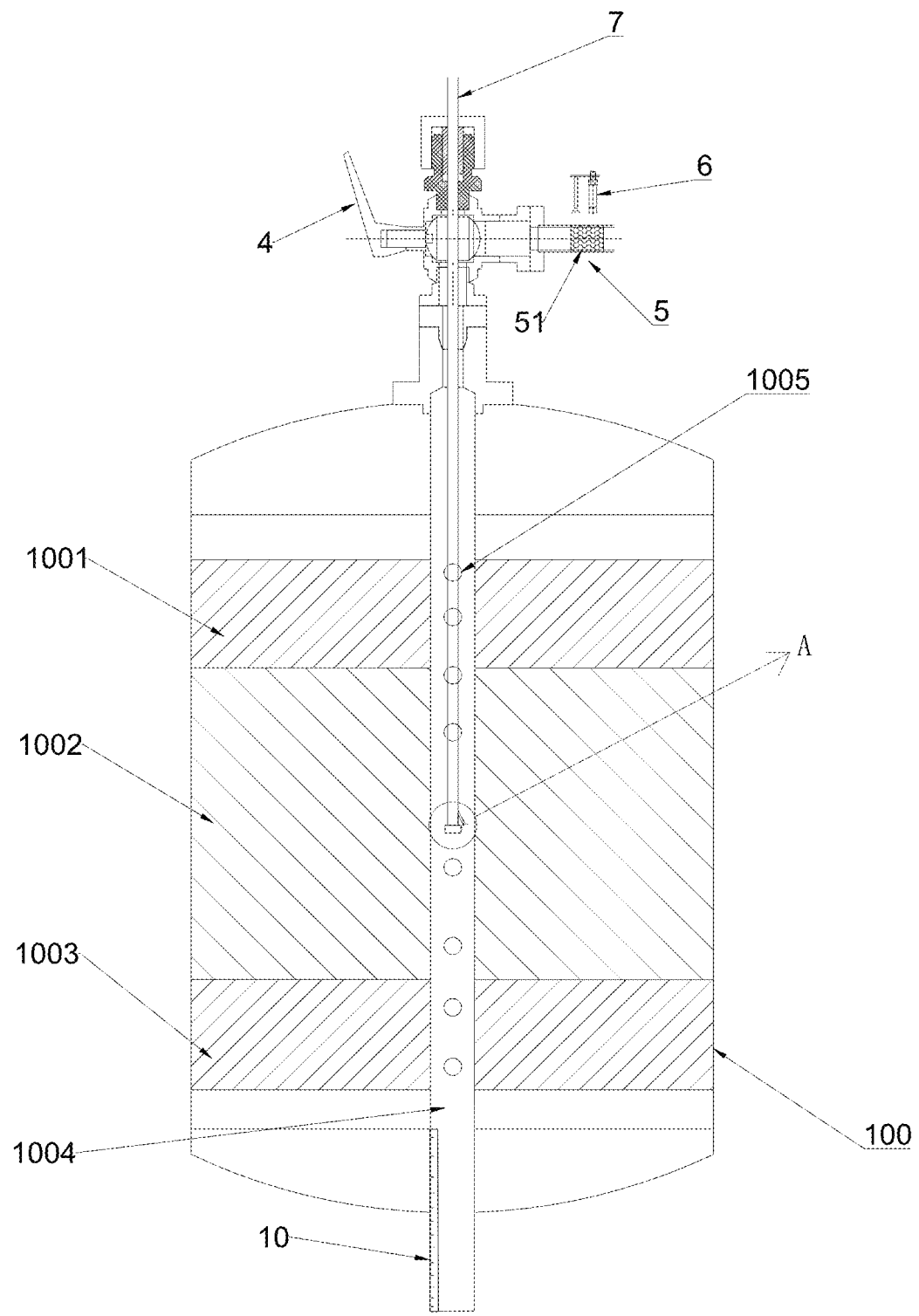
FIG. 4 is a sectional view of a reactor in another embodiment.

Accordingly, in some other embodiments, as shown in FIG. 4, holes 1005 are spacedly disposed along the longitudinal direction of the wellbore 1004 inside the reactor 100. A directional-control ball valve 4 is disposed at an upper portion of the wellbore 1004 outside the reactor 100, and one outlet of the directional-control ball valve 4 is connected with a wellbore discharge pipeline 5, such that it is possible to alter the fluid flow direction inside the wellbore 1004 via the directional-control ball valve 4 and thereby the pipe flow from the wellbore 1004 will be directed to the wellbore discharge pipeline 5. A sight glass 51 is provided on the wellbore discharge pipeline 5, wherein a first camera 6 and a first lamp 11 beside the sight glass 51 for filming the pipe flow inside the wellbore discharge pipeline 5, such that the first camera 6 enables the real-time monitoring of the discharging pipe flow from the wellbore 1004, and thereby realizes the visual inspection on the horizontal pipe flow coming out from the wellbore, which gives flow information of the discharge pipeline during hydrate exploitation, such as: whether the pipe flow contains hydrates, whether the pipe flow contains sands, and sand diameters.

Figure 5:
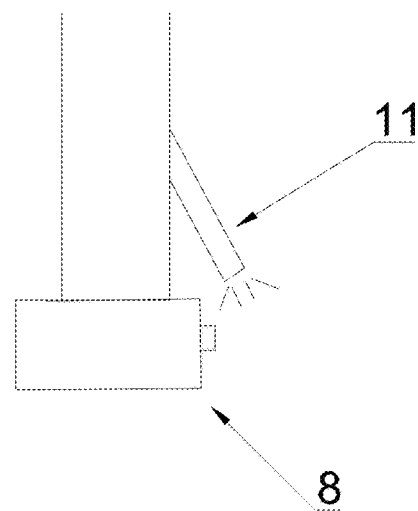
FIG. 5 is an enlarged view of area A in FIG. 4.

Inside the wellbore 1004 is further provided with an endoscopic-camera tube 7, which is disposed inside the wellbore 1004, passing through the directional-control ball valve and extending to the outside of the wellbore 1004, such that the endoscopic-camera tube 7 is able to move up and down and rotate 360 degrees. As shown in FIG. 5, a second camera 8 and a second lamp 9 are provided at the bottom end of the endoscopic-camera tube 7, wherein the second lamp 9 is disposed above the second camera 8 and arranged obliquely, so that the second camera 8 takes clearer videos. Accordingly, by moving the endoscopic-camera tube 7, the second camera 8 and the second lamp 9 can move up and down along with the endoscopic-camera tube 7 inside the wellbore 1004; also, the second camera 8 and the second lamp 9 can rotate 360 degrees. During hydrate exploitation, the visual inspection on the multiphase flow and sand production at any layer and any position can be realized, by moving the second camera 8 and the second lamp 9 with the endoscopic-camera tube 7 to the specific position, where they aim at the hole 1005 of the desired position, and the second lamp 9 provides an oblique light source to help the second camera 8 work. Accordingly, the situation of sand production of each layer can be inspected, such as the sand production time, the occurrence of sand blast, and the volume of sands; also, the camera can rotate to aim at different holes, for observing the situation at each single hole, such as sand production rate and gas production rate. Meanwhile, the second camera 8 and the second lamp 9 can move to where they are required during experiment; they will be moved to the designated observation position when they are needed, while they will be moved to a space above the directional-control ball valve 4 when they are not needed so as to prevent them from affecting the vertical pipe flow and also protect the camera. Moreover, the endoscopic-camera tube can be further provided with other measurement devices, such as an infrared-based device or an ultrasound-based device for measuring the flow rate, to obtain more information inside the wellbore.

In addition, the endoscopic-camera tube 7 can be further provided at its bottom end with a mechanical sensor (not shown in the drawings) which send the monitored data to the computer, such that during sand blast, the mechanical sensor can send sand information to the computer for analysis, giving information such as sand sizes, and thereby realizing the visual inspection of sands. In addition, the well bore 1004 can be further provided, at its section outside the reactor, with a scaled sight glass 10 for observing settled sands, which is made of sapphire and allows to observe the amount of settle sands at the bottom of the wellbore.

During hydrate exploitation, the visual inspection on the multiphase flow and sand production at any layer and any position can be realized, by moving the second camera and the second lamp using the endoscopic-camera tube to the specific position where they aim at the hole of the desired position, so as to realize the real-time inspection on the sand production, gas production, and multiphase flow inside the vertical wellbore.

With the aid of the first lamp, the first camera realizes the real-time monitoring of discharged pipe flow.

The first camera and the second camera send the captured videos to the computer, so as to enable the visual inspection inside the wellbore. During the visual inspection of sand blast, the mechanical sensor sends the sand information to the computer for analysis to give sand sizes, realizing the visual inspection of sands.

The second camera and the second lamp will be moved to a space above the directional-control ball valve when they are not needed, where they will be protected after the directional-control ball valve is switched.

Accordingly, the above-mentioned equipments provided to the reactor allow the visual inspection of natural gas hydrate production, taking videos inside the wellbore, real-time inspection on the multiphase flow inside the wellbore including whether the flow contains hydrate phase and how the flow rate changes. They also allow inspect the sand production of different formation layers, including the sand production time, the occurrence of sand blast, and the volume of sands. They can move to where they are required during experiment; they will be moved to the designated observation position when they are needed, while they will be moved to a space above the directional-control ball valve when they are not needed so as to prevent them from affecting the vertical pipe flow and also protect the camera. They also enable the visual inspection on the horizontal pipe flow coming out from the wellbore, which gives flow information of the discharge pipeline during hydrate exploitation, such as: whether the pipe flow contains hydrates, whether the pipe flow contains sands, and sand diameters. They also enable the inspection of pipe flow of gas phase and water phase.

Furthermore, though the flow filed measurement is useful and necessary for large-scale experimental systems for studying natural gas hydrate, it is still difficult to realize. At present, devices for measuring flow field are mostly designed to allow visual inspection, such as providing optical generators in combination with cameras or disposing visual units such as sight glasses, for observing or filming the change of flow field and thereby realize the measurement of flow field. However, natural gas hydrates are mostly accumulated in porous media, wherein use of sight glasses only enables observation of the porous media, while it is difficult to send a camera deep into a reactor and film in the environment inside the reactor. It is impossible to effectively observe or measure the flow field in the reactor by these means.

Therefore, in some embodiments, the reactor is further provided with a flow field measurement device. As shown in FIG. 6, nine vertical wells are symmetrically distributed throughout each layer. The wells are respectively numbered as 1-A, 2-A, . . . , 9-B, and 9-C, wherein the vertical well 9-B located at center is a central vertical well, while the remaining vertical wells are non-central vertical wells.

Specifically, as shown in FIG. 7, the flow field measurement device comprise non-central vertical well pressure sensors 20, non-central vertical well outlet valves 21, communicating vessel valves 22, differential pressure sensors 23, a communicating vessel 24, a central vertical well outlet valve 25, and a central vertical well pressure sensor 26.

As shown in FIG. 7, all non-central vertical well outlet pipelines 200, except for the vertical well 9-B, are respectively connected to a non-central vertical well pressure sensor 20, a non-central vertical well outlet valve 21, and one end of a differential pressure sensor 23 in sequence. The other end of the differential pressure sensor 23 is connected to a communicating vessel valve 22. All of the communicating vessel valves 22 are connected with the communicating vessel 24. The other end of the communicating vessel 24 is connected to the central vertical well outlet valve 25, the central vertical well pressure sensor 26, and a central vertical well outlet pipeline 27.

The twenty-six differential pressure sensors are respectively numbered as A1, B1, Cl, A2, . . . , A9, and C9, representing the differential pressure sensor connecting the well 1-A and well 9-B, the differential pressure sensor connecting the well 1-B and well 9-B, . . . , the differential pressure sensor connecting the well 9-A and well 9-B, and the differential pressure sensor connecting the well 9-C and well 9-B. Specifically, the differential pressure sensors 23 have a measuring accuracy higher than that of the central vertical well pressure sensor 26 and non-central vertical well pressure sensors 20, and a measuring range lower than that of the central vertical well pressure sensor 26 and non-central vertical well pressure sensors 20. Since the pressure sensors are not applicable for low pressure differences due to their low measuring accuracy while the differential pressure sensors 23 have a higher measuring accuracy, when the pressure difference is relatively low, the pressure sensors may show the same readings while the differential pressure sensors is capable of revealing the pressure difference; when the pressure difference is relatively high and exceed the measuring range of the differential pressure sensors, the differential pressure sensors may be damaged. In summary, the differential pressure sensors have a high accuracy but a low measuring range, while the pressure sensors have a high measuring range but a low accuracy, and thus these two kinds of sensors should be used in combination.

Accordingly, when it is necessary to inspect a flow field in the reactor, the first step is recording readings of the twenty-seven pressure sensors to obtain a pressure difference between each vertical well and the central vertical well, and then comparing the obtained pressure difference with a measuring range of the differential pressure sensor; if the obtained pressure difference is higher than the measuring range of the differential pressure sensor, then the obtained pressure difference is determined to be a pressure difference between the non-central vertical well corresponding to the differential pressure sensor and the central vertical well; if the obtained pressure difference is not higher than the measuring range of the differential pressure sensor, then opening the non-central vertical well outlet valve and the communicating vessel valve which are connected to the differential pressure sensor, and measuring the pressure difference between the corresponding non-central vertical well and the central vertical well using the differential pressure sensor. Driven by the pressure differences, gas and liquid will flow spontaneously from a high pressure zone to a low pressure zone (or tend to flow spontaneously from the high pressure zone to the low pressure zone), in other words, the accurate measurement of flow field in the reactor is realized.

In view of the above, with the flow field measurement device, the flow field inside the reactor is quantified according to the pressure differences between the points, accurately and effectively. Providing differential pressure sensors, between a measuring point of the central vertical well and a measuring point of each of the non-central vertical wells, to measure the pressure differences, enables reasonable distribution of three-dimensional space inside the entire reactor, making it easier to analyze the gas-liquid flow trends in the reactor with the simulated flow field. The step of determining whether to turn on the differential pressure sensors according to a predetermination based on the feedback from the pressure sensors, allows flow field measurements in the reactor under both high and low pressure differences and effective protection of the differential pressure sensors. Meanwhile, since communication of the entire measurement device is realized by the vertical well outlet pipelines, the measurement device can be externally connected to the reactor, in other words, the differential pressure sensors and the communicating vessel can be disposed outside the reactor. Thus, it is not necessary to conduct significant modifications to the entire gas hydrate system, and no damage will be done to the experimental devices; for a natural gas hydrate experimental system without flow field measurement function, it is possible to introduce the present device whenever it is required.

Specifically, a data output of each of the non-central vertical well pressure sensors 20, the central vertical well pressure sensor 26, and the differential pressure sensors 23 is connected to a data collecting-processing-displaying module 4. With such configuration, the data collecting-processing-displaying module 4 enables the real-time display of the recorded data, so as to realize the real-time measurements of flow field in the reactor.

Preferably, the communicating vessel 24 is further provided with a communicating vessel pressure sensor 28 and a gas injection valve 29. Such configuration allows testing the differential pressure sensors 23 using the gas injection valve 29. The method are as follows: closing the non-central vertical well outlet valves, such that the differential pressure sensors show a same reading at their ends connected to the non-central vertical well outlet valves; connecting the gas injection valve of the communicating vessel to a gas cylinder with a given pressure lower than the measuring range of the differential pressure sensors; opening the communicating vessel valves, and opening a valve of the gas cylinder, and recording readings of the differential pressure sensors. Normally, the readings of the differential pressure sensors should be identical; a differential pressure sensor that shows no reading or a significantly different reading requires replacement or repair.

In view of the above, through the technical solutions as disclosed in FIG. 6 and FIG. 7, compare with the prior art, the device has the following technical advantages:

(1) The pressure sensors and the differential pressure sensors are connected to the data collecting-processing-displaying module, which realizes the real-time measurements of flow field in the reactor.

(2) The flow field inside the reactor is quantified according to the pressure differences between the points in the reactor, accurately and effectively.

(3) Providing differential pressure sensors, between a measuring point of the central vertical well and a measuring point of each of the non-central vertical wells, to measure the pressure differences, enables reasonable distribution of three-dimensional space inside the entire reactor, making it easier to analyze the gas-liquid flow trends in the reactor with the simulated flow field.

(4) The step of determining whether to turn on the differential pressure sensors according to a predetermination based on the feedback from the pressure sensors, allows flow field measurements in the reactor under both high and low pressure differences and effective protection of the differential pressure sensors.

(5) The differential pressure sensors are externally disposed for flow field measurements in the reactor; such design will not affect the natural gas hydrate experiment.

(6) It is not necessary to conduct significant modifications to the entire gas hydrate system, and no damage will be done to the experimental devices; for a natural gas hydrate experimental system without flow field measurement function, it is possible to introduce the present device whenever it is required.

(7) Design of the communicating vessel allows testing the differential pressure sensors regardless of the natural gas hydrate experimental system, and thereby the operation is simple, safe, and reliable.

The above-mentioned embodiments are only intended to illustrate the technical concept and characteristics of the present invention, enabling those of ordinary skill in the art to understand the content of the present invention and implement them accordingly, but are not intended to limit the scope of the present invention. All equivalent changes or modifications made according to the essence of the present invention should fall within the scope of the present invention.

What is claimed is:

1. A device for measuring stratum deformation caused by natural gas hydrate dissociation, wherein the device is configured to be disposed inside a reactor, wherein the reactor is configured to simulate natural gas hydrate formation layers, and the natural gas hydrate formation layers comprise a superstratum layer, a sediment layer and a substratum layer from top to bottom, wherein the device comprises a displacement sensor fixing plate, a plurality of displacement sensors and an elastic plate; wherein a first end of each displacement sensor is fixed to the displacement sensor fixing plate and a second end of each displacement sensor is fixed to the elastic plate; the elastic plate is attached to the superstratum layer, and the displacement sensor fixing plate is fixedly disposed in the reactor;

wherein the elastic plate is a rubber piston, and the rubber piston comprises a piston frame, a rubber piston plate, a rubber insert, a piston gasket, and a clip, wherein a periphery of the rubber piston plate is fixed to the piston frame; the piston gasket is embedded in a groove of the piston frame; the periphery of the rubber piston plate is fixed to a lower surface of the piston frame through the rubber insert the clip is embedded between the rubber insert and the lower surface of the piston frame, and the clip is configured to connect the piston frame to the rubber piston plate.

2. The device according to claim 1, wherein the device comprises an intelligent terminal, wherein data collected by the each displacement sensor is transmitted to the intelligent terminal.

3. The device according to claim 2, wherein the intelligent terminal is a computer, a tablet computer, or a mobile phone.

4. The device according to claim 1, wherein the plurality of displacement sensors are linear variable differential transformer (LVDT) displacement sensors.

5. The device according to claim 1, wherein the clip is made of a non-metallic material.

* * * * *